US00PP34312P2

(12) United States Plant Patent
Hansen

(10) Patent No.: US PP34,312 P2
(45) Date of Patent: Jun. 7, 2022

(54) ***HOSTA* PLANT NAMED 'EMPEROR'S NEW CLOTHES'**

(50) Latin Name: ***Hosta* hybrid (Tratt.)**
Varietal Denomination: Emperor's New Clothes

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 17/803,080

(22) Filed: Feb. 1, 2022

(51) Int. Cl.
*A01H 6/12* (2018.01)
*A01H 5/02* (2018.01)

(52) U.S. Cl.
USPC ..... Plt./353

(58) Field of Classification Search
USPC ..... Plt./353
See application file for complete search history.

*Primary Examiner* — Annette H Para

(57) ABSTRACT

A new and distinct *Hosta* plant named 'Emperor's New Clothes' with large-sized, rounded-mound habit of large ovate to nearly cordate foliage. Leaves begin the season with a yellowish-green with dark-green speckles, patches and streaks and mature to a minty green from tiny speckling on a white background, with patches and streaks of dark-green. The plant produces pale purple flared campanulate flowers on upright scapes well above the foliage beginning in mid-June and continuing for about four weeks.

3 Drawing Sheets

Latin name and variety denomination of the plant: Botanical classification: *Hosta* hybrid (Tratt.).
Variety denomination: 'Emperor's New Clothes'.

STATEMENT REGARDING PRIOR DISCLOSURES UNDER 37 CFR 1.77(b)(6)

The non-enabling disclosure of the claimed plant, in the form of cultivar registration with The American *Hosta* Society which is the International Cultivar Registration Authority for the genus *Hosta* was by the inventor in December 2021 with public internet posting in early 2022. No plants of *Hosta* 'Emperor's New Clothes' have been sold, in this country or anywhere in the world, nor has any disclosure of the new plant been made, more than one year prior the filing date of this application, and such sale or disclosure within one year was either derived directly or indirectly from the inventor.

BACKGROUND AND ORIGIN OF THE PLANT

The present invention relates to a new and distinct *Hosta* plant, *Hosta* 'Emperor's New Clothes' hereinafter also referred to as the new plant or just the cultivar name, 'Emperor's New Clothes'. *Hosta* 'Emperor's New Clothes' was discovered by the inventor on Mar. 8, 2018 at a wholesale perennial nursery greenhouse in Zeeland, Mich., USA as a whole plant mutation in a tissue-cultured batch of 'Empress Wu' U.S. Plant Pat. No. 20,774, and was give the breeder code 18-SP-HOST-645. The new plant was approved for final selection in the spring of 2021. The new plant has been asexually propagated by division at the same nursery in Zeeland, Mich., USA since 2020 with the resultant asexually propagated plants having retained all the same traits as the original plant. *Hosta* 'Emperor's New Clothes' is stable and reproduces true to type in asexual reproduction.

BRIEF SUMMARY OF THE PLANT

There are nearly 7,000 registered *Hosta* cultivars with The American *Hosta* Society, which is the International Cultivar Registration Authority for the genus *Hosta* along with a similar number of unregistered cultivars. The nearest comparison varieties are: 'Allegan Fog' (not patented), 'Spilt Milk' (not patented), 'London Fog' (not patented), 'American Hero' (not patented), 'Revolution' (not patented), 'Lakeside Zing Zang' (not patented), 'Nougat' (not patented), 'Masquerade' (not patented) and 'Gunther's Prize' (not patented).

'Allegan Fog' has a smaller habit and leaves are smaller with a dark green margin and smaller green speckles in the creamy white center. 'Spilt Milk' has thicker blue-green foliage that has linear speckles or short streaks of white. 'London Fog' has a smaller habit with narrower foliage having a smaller speckles of green in a greenish-white leaf. 'American Hero' has a smaller habit with more twisted foliage that has a wide deep-green margin and green speckles in a creamy-white center. 'Revolution' has a smaller habit with more lustrous foliage that has a wide deep-green margin and green speckles in a creamy-white center and shorter leaf blades that have a coarser marginal wave. 'Lakeside Zing Zang', 'Nougat', and 'Masquerade' are all significantly smaller in habit and leaf size, the leaves are more narrow lanceolate-shaped. 'Nougat' does not have a green margin whereas 'Lakeside Zing Zang' and 'Masquerade' have narrow green margins on the leaves. All of the above have speckles that are smaller than the new plant. 'Gunther's Prize' is a large yellowish leaf with large chartreuse to medium green speckles and streaks, the flower stalks are more arching to nearly horizontal and the flower shape is not as widely flared and the flower color a deeper lavender purple in the center of the tepals.

The parent of the sport, 'Empress Wu', has solid dark green leaves without the white background and large green speckles. Other similarly related known cultivars include 'Wu-La-La' U.S. Plant Pat. No. 31,309, that has a deep green center and yellowish margin and lacks the light base with dark green patches and speckles.

*Hosta* 'Emperor's New Clothes' is distinct from the *Hostas* listed above and all other cultivars known to the hybridizer by the following combined traits:

1. Large-sized, rounded-mound plant habit with outwardly, glaucous foliage becoming dull to slightly shiny on top;
2. Foliage is large, ovate to nearly cordate that is typically flat;
3. Foliage is variegated with yellowish green with dark-green speckles, patches and streaks in the spring
4. Foliage becomes minty-green in the late season from the numerous dark-green tiny speckles and has dark-green patches and streaks;
5. Pale purple, flared, campanulate flowers, well above the foliage, densely arranged, on numerous arching scapes beginning in mid-June for about four weeks.

BRIEF DESCRIPTION OF THE DRAWINGS

The photographs of the new plant demonstrate the overall appearance of a three-year-old plant, including the unique traits of 'Emperor's New Clothes'. The colors are as accurate as reasonably possible with color reproductions. Ambient light spectrum, temperature, source and direction may cause the appearance of minor variation in color.

DETAILED BOTANICAL DESCRIPTION

Figure 1:
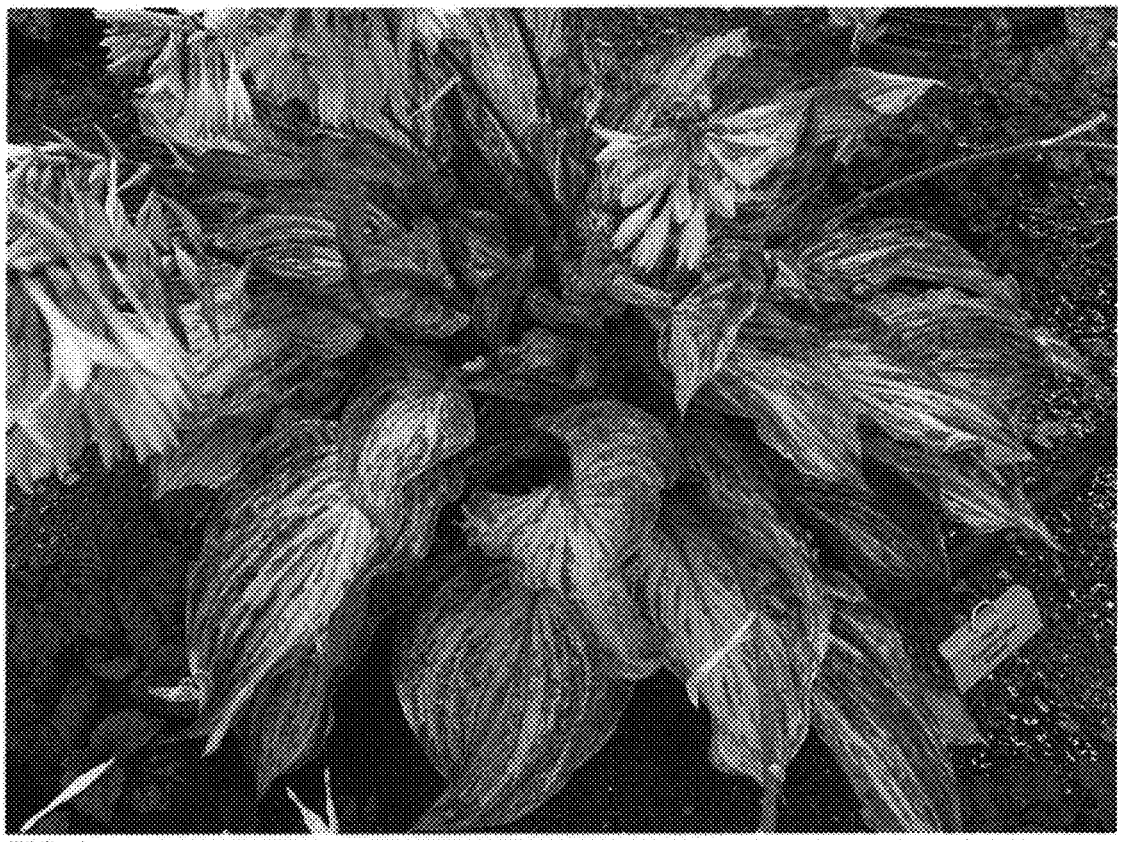
FIG. 1 shows a plant grown in a shaded trial garden in peak mid-summer flowering.
Figure 2:
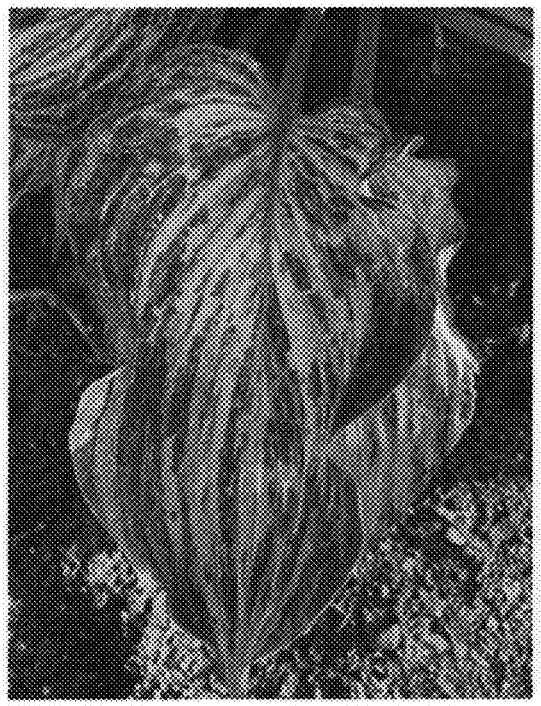
FIG. 2 shows a close-up of a leaf in early season prior to flowering.
Figure 3:
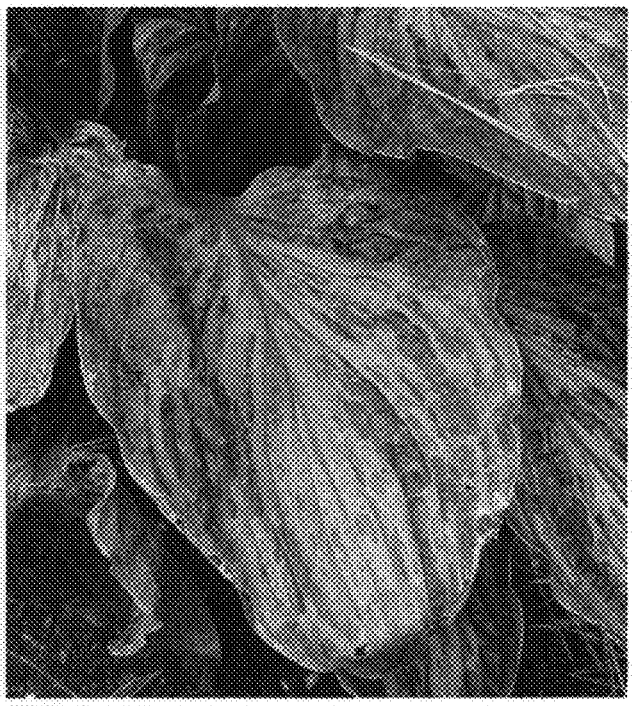
FIG. 3 shows a close-up of leaf in late season.
Figure 4:
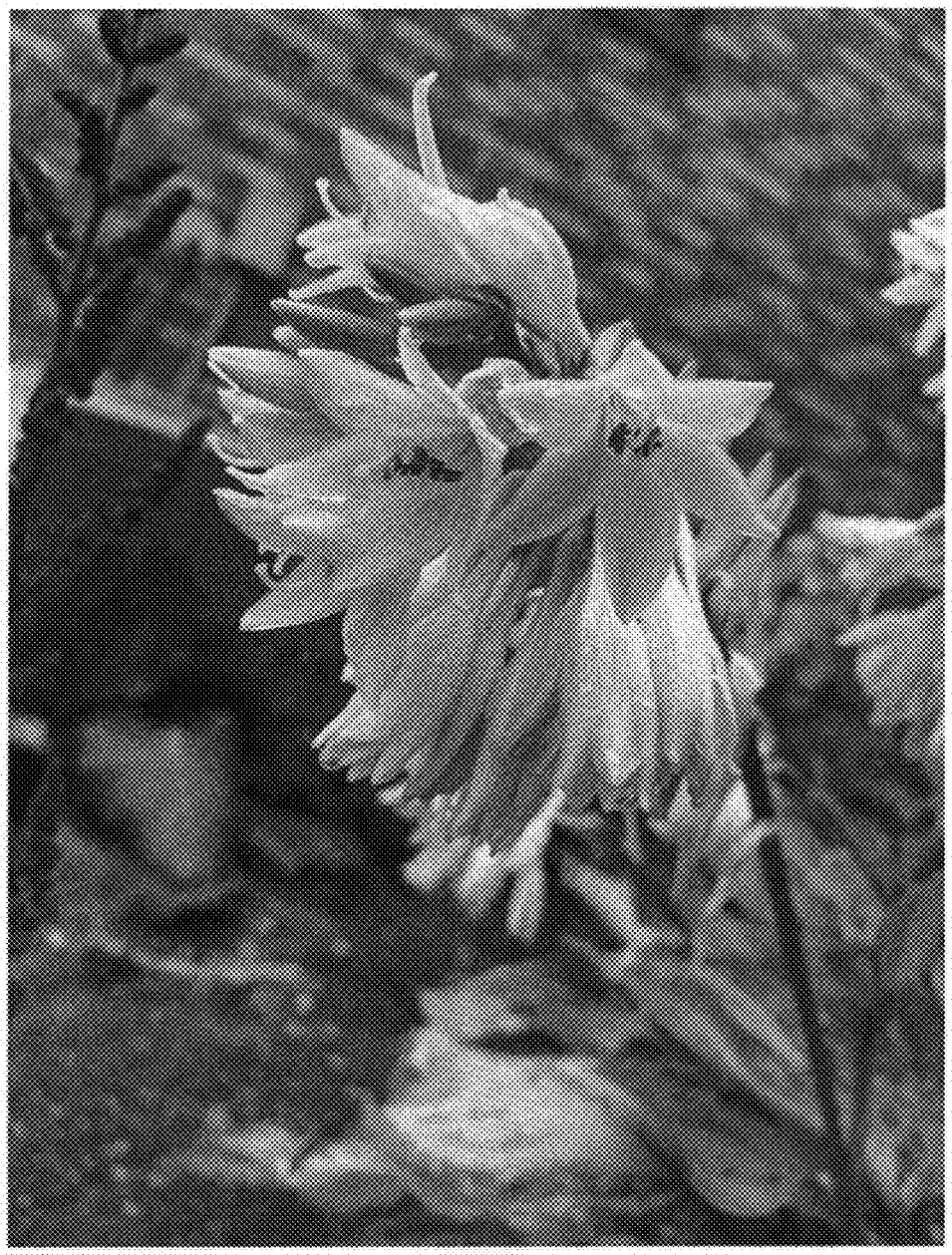
FIG. 4 shows the flowering scape of the new plant with open flowers and young buds.

The following descriptions and color references are based on the 2015 edition of The Royal Horticultural Society Colour Chart except where common dictionary terms are used. The new plant, *Hosta* 'Emperor's New Clothes', has not been observed under all possible environments. The phenotype may vary slightly with different environmental conditions, such as temperature, light, fertility, moisture and maturity levels, but without any change in the genotype. The following observations and size descriptions are of a three-year-old plant in a shaded trial garden in Zeeland, Mich. with supplemental water and fertilizer.

Botanical classification: *Hosta* hybrid.

Parentage: The parent plant is 'Empress Wu'.

Propagation: Garden division.

Growth rate: Moderate to rapid.

Crop time: About 2 to 3 months to finish during the summer in a one-liter container from rooted tissue culture plantlet.

Rooting habit: Normal, fleshy, lightly branching.

Root color: Variable, nearest RHS 164D to RHS 158D depending on soil type.

Plant shape and habit: Hardy herbaceous perennial with basal rosette of mostly outwardly pointed leaves emerging from rhizomes producing a large symmetrical rounded-mound of leaves.

Plant size: Foliage height to about 53.3 cm from the soil line to the top of the leaves and about 104 cm wide at the widest point slightly above the soil line.

Foliage description: Ovate to nearly cordate; glabrous, top surface begins season slightly glaucous becoming dull matte surfaced to slightly shiny, and bottom surface is glaucous and tends to stay through most of the season; margin entire and moderately sinuate; narrowly acute and twisted apex with attenuate base; with slightly impressed veins.

Leaf blade size: To about 22.9 cm long and 15.2 cm wide; width to length ration of about 1:1.5 but typically becomes broader with maturity; with patches and speckles of various sizes of between 0.5 mm diameter and 6.0 cm long and 1.5 cm across.

Leaf blade color: Early season and shortly after emerging variable, adaxial between RHS 145D and RHS 150D with irregularly-sized and shaped patches and speckles of variable green colors comprising RHS NN137A, N138A, RHS 144A and between RHS N138D and RHS 189B, abaxial nearest RHS 150D with irregular patches and speckles comprising RHS 191C and RHS N138D; late summer to early tall adaxial main color a mist whitish-green between RHS NN155C and RHS NN155D having a minute speckling of nearest RHS 137A with irregular patches and streaks of variable green colors comprising nearest RHS 144A and between RHS N138A and RHS 189A, late summer to early fall abaxial main color between RHS 188D and RHS NN155D with speckles or variably-sized patches of nearest 189B and RHS 194B.

Petiole: Glabrous; slightly glaucous; concavo-convex; mostly straight from base of plant to leaf blade; to about 33 cm long and at base 19 mm across about 5 cm above the soil.

Petiole color: Early season adaxial distally between RHS 139B and RHS 139C with minute speckles less than 1 mm nearest RHS 139B, abaxial nearest RHS 138C; late summer to fall adaxial nearest RHS N147A and abaxial distally nearest RHS 138D.

Veins: Parallel; only lightly impressed adaxial, slightly costate abaxial; 13 to 14 pairs with one midrib.

Veins color: Adaxial nearest RHS 145A; abaxial nearest RHS 145C with abaxial midrib nearest RHS 145D.

Flower description:

Buds: One day prior to opening clavate with acute apex gradually tapering to a long thin corolla tube and rounded base; nearest RHS 91D in basal portion and RHS 92D at middle and apex; to about 38 mm long, and 7 mm wide at the broadest portion, corolla tube portion to about 15 mm and 3 mm diameter.

Bud color: Nearest RHS 91D at base and RHS 92D at middle and apex.

Flowers: 28 to 34 per scape; tightly arranged with about 6 to 8 flowers per 1 cm centimeter of scape in some areas and spaced 1 cm apart in other areas; funnelform; about 32 mm wide and 51 mm long to exserted stigma, (distal flowers opening smaller); remain open for a normal period, usually one to two days on or cut from plant; scapes remain effective from mid-June into mid-July in Zeeland, Mich.; no detectable fragrance.

Tepal: Two nearly identical sets of three fused at the basal two thirds; acute apex; margins entire; approximately 47 mm long and 8 mm wide (outer set) 47 mm long and 9 mm wide (inner set).

Tepal color: Adaxial outer set lighter than RHS 76D on margin and center nearest RHS 76C with veins between RHS 76B and RHS 76A, abaxial nearest RHS 76D; adaxial inner set lighter than RHS 76D on margin, center nearest RHS 76C and veins nearest RHS 76A, abaxial nearest RHS 76D.

Pedicel: Cylindrical; glaucous; approximately 13 mm long, 1.5 mm wide; attitude mostly outwardly.

Pedicel color: Distally nearest RHS NN155A and proximally nearest RHS 150D.

Peduncle: Cylindrical; glaucous; usually one per division, erect to slightly arching, about 9 mm diameter at base, average 82 cm tall.

Peduncle color: Nearest RHS N138B.

Gynoecium: Single; superior; about 51 mm long.

Style: About 44 mm long, 1 mm diameter, curled upward at distal 10 mm; color base nearest RHS 145D, nearest RHS NN155D in distal 12 mm.

Stigma: 1.5 mm diameter; pubcrulcnt; color nearest RHS NN155D.

Ovary: Fluted longitudinally; ellipsoidal; to about 5 mm long and 3 mm across; color nearest RHS 146D.

Androecium: Six.

Filaments: Six; about 0.5 mm in diameter and 47 mm long, curving upward the last 1.0 cm; nearest RHS NN155D distally and between RHS 145D and RHS NN155D proximally.

Anthers: Oblong; dorsifixed; longitudinal; about 4 mm long and 1.5 mm wide; dorsal color between RHS N187C and lighter than RHS N77D, ventral between RHS 177A and RHS 177B.

Pollen: Elliptical, less than 0.1 mm long, nearest RHS 13B.

Bracts: Subtending one or more flowers; lanceolate; widest at base and tapering to acute apex; truncate sessile base; margin entire; protruding upward about 80-degree angle away from scape; average about 17 mm long and 7 mm wide in middle; decreasing distally and increasing proximally in both length and width.

Bract color: Young bracts adaxial between RHS 146D and RHS 160D, abaxial nearest RHS 146D with a moderate blush of nearest RHS 146B; near flower opening adaxial between RHS 160D and RHS 157B, abaxial adaxial between RHS 160D and RHS 157B with light blush of nearest RHS 76C.

Fruit: Rare; tri-valved dehiscent capsule; oblong; apiculate apex and truncate base; lightly furrowed; about 22 mm long and 5 mm diameter; color as developing nearest RHS 137A, if maturity reached between RHS 164C and RHS 164D.

Seed: Typically few per capsule under pollination attempts; endospermic; flattened-elliptic wing surrounding embryo situated toward one end of ellipse; up to 5 mm long and 1.5 mm wide and 1 mm thick at embryo; color nearest RHS 202A.

Disease tolerance and resistance: *Hosta* 'Emperor's New Clothes' has not shown any resistance or susceptibility to pests and diseases except that common to *Hostas*.

Growth: The new plant grows best and shows best coloration with plenty of moisture, adequate drainage and light shade, but is able to tolerate some drought when mature.

Hardiness: At least from USDA zone 3 through 9.

It is claimed:

1. A new and distinct ornamental *Hosta* plant named 'Emperor's New Clothes' as herein described and illustrated.

* * * * *